(12) United States Patent
Qazi et al.

(10) Patent No.: US 7,070,814 B2
(45) Date of Patent: Jul. 4, 2006

(54) **BIOAVAILABILITY / BIOEFFICACY ENHANCING ACTIVITY OF *CUMINUM CYMINUM* AND EXTRACTS AND FRACTIONS THEREOF**

(75) Inventors: Ghulam Nabi Qazi, Jammu (IN); Kasturi Lal Bedi, Jammu (IN); Rakesh Kamal Johri, Jammu (IN); Manoj Kumar Tikoo, Jammu (IN); Ashok Kumar Tikoo, Jammu (IN); Subhash Chander Sharma, Jammu (IN); Sheikh Tasaduq Absullah, Jammu (IN); Om Parkash Suri, Jammu (IN); Bishan Datt Gupta, Jammu (IN); Krishan Avtar Suri, Jammu (IN); Naresh Kumar Satti, Jammu (IN); Ravi Kant Khajuria, Jammu (IN); Surjit Singh, Jammu (IN); Anamika Khajuria, Jammu (IN); Bal Krishan Kapahi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/386,395

(22) Filed: Mar. 11, 2003

(65) Prior Publication Data
US 2004/0052873 A1    Mar. 18, 2004

Related U.S. Application Data

(60) Provisional application No. 60/363,460, filed on Mar. 12, 2002.

(51) Int. Cl.
*A61K 35/78* (2006.01)
(52) U.S. Cl. .................. 424/725; 424/776; 424/737
(58) Field of Classification Search ............. 424/195.1, 424/725
See application file for complete search history.

(56) References Cited

U.S. PATENT DOCUMENTS

2004/0121028 A1* 6/2004 Qazi et al. ................. 424/756
2004/0198672 A1* 10/2004 Qazi et al. ................. 514/27

OTHER PUBLICATIONS

Lamb Hayes: Super Stews; Country Living; Newy York: vol. 22, Iss. 1, pp. 1-8 of Proquest direct print-out.*

* cited by examiner

*Primary Examiner*—Christopher R. Tate
(74) *Attorney, Agent, or Firm*—Ladas & Parry LLP

(57) ABSTRACT

The present invention relates to a bioenhancing/bioavailability-facilitating composition comprising:
an effective amount of an extract and/or at least one bioactive fraction from *Cuminum cyminum;*
one or more additive selected from drugs, nutrients, vitamins, nutraceuticals, herbal drugs/products, micro nutrients, antioxidants along with pharmaceutically acceptable additives/excipient, and
optionally, an effective amount of piperine or extract/ fraction of *piper nigrum* or *piper longum;* and
a process for the preparation of such extracts and active fractions from plant *Cuminum cyminum.*

38 Claims, 14 Drawing Sheets

1:271 nm, 8 nm

| Pk # | Retention Time | Area | Area Percent | Height | Height Percent |
|---|---|---|---|---|---|
| 1 | 2.165 | 659977 | 11.25 | 57947 | 12.55 |
| 2 | 2.443 | 428209 | 7.30 | 80897 | 17.53 |
| 3 | 2.752 | 250159 | 4.43 | 34031 | 7.40 |
| 4 | 2.869 | 159497 | 2.72 | 20214 | 4.35 |
| 5 | 3.072 | 55756 | 0.95 | 8405 | 1.83 |
| 6 | 3.243 | 193219 | 3.29 | 16299 | 3.54 |
| 7 | 3.520 | 54461 | 0.93 | 5242 | 1.35 |
| 8 | 3.619 | 124682 | 2.13 | 8711 | 1.89 |
| 9 | 4.075 | 51335 | 0.88 | 4510 | 0.92 |
| 10 | 4.405 | 622258 | 10.51 | 57005 | 12.39 |
| 11 | 4.939 | 45243 | 0.77 | 3836 | 0.53 |
| 12 | 5.237 | 96544 | 1.65 | 5754 | 1.25 |
| 13 | 5.557 | 167865 | 2.86 | 11980 | 2.50 |
| 14 | 6.560 | 850542 | 14.67 | 59426 | 12.92 |
| 15 | 7.221 | 25348 | 0.45 | 1925 | 0.42 |
| 16 | 7.548 | 132237 | 2.25 | 7016 | 1.52 |
| 17 | 8.277 | 423786 | 7.22 | 21828 | 4.74 |
| 18 | 8.896 | 113164 | 1.93 | 6328 | 1.13 |
| 19 | 9.312 | 34999 | 0.50 | 1706 | 0.37 |
| 20 | 10.464 | 233860 | 3.99 | 8250 | 1.80 |
| 21 | 10.380 | 9477 | 0.15 | 555 | 0.12 |
| 22 | 11.243 | 12204 | 0.21 | 533 | 0.12 |
| 23 | 11.737 | 6842 | 0.12 | 421 | 0.09 |
| 24 | 11.979 | 7513 | 0.13 | 420 | 0.09 |
| 25 | 12.971 | 51235 | 0.37 | 1209 | 0.25 |
| 26 | 14.347 | 541450 | 9.23 | 20087 | 4.37 |
| 27 | 15.243 | 389015 | 0.60 | 11422 | 2.43 |
| 28 | 17.003 | 29871 | 0.51 | 757 | 0.15 |
| 29 | 17.824 | 17812 | 0.30 | 695 | 0.15 |
| 30 | 18.475 | 2896 | 0.05 | 108 | 0.02 |
| 31 | 18.923 | 86 | 0.00 | 23 | 0.00 |
| 32 | 19.477 | 2171 | 0.04 | 120 | 0.03 |
| 33 | 21.855 | 4701 | 0.08 | 149 | 0.03 |
| 34 | 23.381 | 44527 | 0.75 | 1134 | 0.25 |
| 35 | 24.875 | 2516 | 0.04 | 125 | 0.03 |
| Totals | | 5865707 | 100.00 | 450078 | 100.00 |

| Pk # | Retention Time | Area | Area Percent | Height | Height Percent |
|---|---|---|---|---|---|
| 1 | 2.133 | 519125 | 6.37 | 34166 | 5.21 |
| 2 | 2.432 | 428631 | 5.25 | 46755 | 8.50 |
| 3 | 2.741 | 448350 | 5.50 | 47792 | 8.59 |
| 4 | 2.859 | 300873 | 3.69 | 29195 | 5.31 |
| 5 | 3.221 | 254333 | 3.24 | 23991 | 4.35 |
| 6 | 3.509 | 69158 | 0.85 | 7163 | 1.30 |
| 7 | 3.797 | 130394 | 1.50 | 9942 | 1.81 |
| 8 | 4.032 | 52033 | 0.64 | 4751 | 0.85 |
| 9 | 4.384 | 825295 | 10.14 | 77951 | 14.12 |
| 10 | 4.917 | 41721 | 0.51 | 3724 | 0.58 |
| 11 | 5.216 | 123183 | 1.51 | 7691 | 1.40 |
| 12 | 5.579 | 177979 | 2.18 | 13332 | 2.42 |
| 13 | 6.539 | 1129188 | 13.85 | 81297 | 14.75 |
| 14 | 7.189 | 22492 | 0.28 | 1743 | 0.32 |
| 15 | 7.527 | 151874 | 1.86 | 8678 | 1.53 |
| 16 | 8.256 | 868364 | 10.55 | 51361 | 9.34 |
| 17 | 8.875 | 145756 | 1.79 | 8578 | 1.52 |
| 18 | 9.323 | 44868 | 0.55 | 1998 | 0.36 |
| 19 | 10.432 | 315535 | 3.87 | 13074 | 2.38 |
| 20 | 10.944 | 227 | 0.00 | 43 | 0.01 |
| 21 | 12.907 | 36375 | 0.45 | 1402 | 0.25 |
| 22 | 14.293 | 1205906 | 14.79 | 47925 | 3.72 |
| 23 | 15.179 | 551219 | 7.99 | 21401 | 3.89 |
| 24 | 15.949 | 41949 | 0.51 | 1133 | 0.21 |
| 25 | 17.792 | 22275 | 0.27 | 895 | 0.16 |
| 26 | 18.411 | 5531 | 0.07 | 163 | 0.03 |
| 27 | 18.912 | 1174 | 0.01 | 98 | 0.02 |
| 28 | 19.317 | 3915 | 0.05 | 117 | 0.02 |
| 29 | 20.575 | 8184 | 0.10 | 289 | 0.05 |
| 30 | 21.835 | 10738 | 0.13 | 297 | 0.05 |
| 31 | 23.339 | 95980 | 1.18 | 2380 | 0.43 |
| 32 | 24.811 | 9097 | 0.11 | 387 | 0.07 |
| Totals | | 8152723 | 100.00 | 549814 | 100.00 |

| Pk # | Retention Time | Area | Area Percent |
|---|---|---|---|
| 1 | 0.992 | 2001 | 0.02 |
| 2 | 1.277 | 389 | 0.00 |
| 3 | 1.845 | 7829 | 0.08 |
| 4 | 2.529 | 2314004 | 22.30 |
| 5 | 3.104 | 274340 | 2.54 |
| 6 | 3.595 | 1115233 | 10.75 |
| 7 | 4.512 | 1249257 | 12.04 |
| 8 | 6.432 | 254283 | 2.45 |
| 9 | 8.256 | 1997505 | 19.25 |
| 10 | 11.019 | 2490410 | 24.00 |
| 11 | 14.464 | 671723 | 6.47 |
| Totals | | 10377044 | 100.00 |

F I G. 3B

1:271 nm, 8 nm

| Pk # | Retention Time | Area | Area Percent | Height | Height Percent |
|---|---|---|---|---|---|
| 1 | 1.675 | 448667 | 7.58 | 48054 | 10.40 |
| 2 | 2.016 | 501850 | 8.48 | 44875 | 9.72 |
| 3 | 2.155 | 838979 | 14.18 | 59346 | 12.65 |
| 4 | 2.432 | 694020 | 11.73 | 51581 | 13.33 |
| 5 | 2.752 | 207632 | 3.51 | 34703 | 7.50 |
| 6 | 2.859 | 306667 | 5.18 | 25002 | 5.63 |
| 7 | 3.253 | 160697 | 2.72 | 12425 | 2.59 |
| 8 | 3.499 | 98743 | 1.67 | 7779 | 1.58 |
| 9 | 3.808 | 95225 | 1.61 | 7955 | 1.72 |
| 10 | 4.064 | 42473 | 0.72 | 4300 | 0.93 |
| 11 | 4.384 | 593463 | 10.03 | 54167 | 11.73 |
| 12 | 4.917 | 52937 | 0.89 | 3842 | 0.83 |
| 13 | 5.205 | 72082 | 1.22 | 3886 | 0.84 |
| 14 | 5.600 | 63479 | 1.07 | 3369 | 0.73 |
| 15 | 5.973 | 22533 | 0.38 | 1827 | 0.40 |
| 16 | 6.528 | 712788 | 12.05 | 52884 | 11.45 |
| 17 | 7.179 | 21776 | 0.37 | 1735 | 0.38 |
| 18 | 7.616 | 124655 | 2.11 | 6506 | 1.41 |
| 19 | 8.224 | 168980 | 2.85 | 7245 | 1.57 |
| 20 | 8.843 | 35961 | 0.51 | 1896 | 0.41 |
| 21 | 9.259 | 17602 | 0.30 | 785 | 0.17 |
| 22 | 9.952 | 29290 | 0.50 | 878 | 0.19 |
| 23 | 10.421 | 22373 | 0.38 | 1075 | 0.23 |
| 24 | 11.516 | 158688 | 2.85 | 2010 | 0.44 |
| 25 | 12.800 | 39049 | 0.65 | 1121 | 0.24 |
| 26 | 14.251 | 178355 | 3.01 | 5941 | 1.29 |
| 27 | 15.157 | 161212 | 2.72 | 4725 | 1.02 |
| 28 | 16.768 | 19071 | 0.32 | 443 | 0.10 |
| 29 | 17.726 | 3256 | 0.07 | 152 | 0.03 |
| 30 | 23.221 | 11273 | 0.19 | 256 | 0.05 |
| 31 | 24.583 | 2361 | 0.04 | 102 | 0.02 |
| Totals | | 5916848 | 100.00 | 461878 | 100.00 |

| Pk # | Retention Time | Area | Area Percent |
|---|---|---|---|
| 1 | 0.288 | 236 | 0.00 |
| 2 | 1,792 | 36496 | 0.41 |
| 3 | 2.464 | 998437 | 11.27 |
| 4 | 3.115 | 1353042 | 15.27 |
| 5 | 4.171 | 551368 | 6.22 |
| 6 | 5.280 | 384641 | 4.34 |
| 7 | 6.112 | 236699 | 2.67 |
| 8 | 7.755 | 976908 | 11.03 |
| 9 | 10.379 | 1100982 | 12.43 |
| 10 | 13.803 | 926759 | 10.46 |
| 11 | 17.952 | 1770430 | 19.99 |
| 12 | 20.949 | 520250 | 5.87 |
| 13 | 25.944 | 1246 | 0.01 |
| 14 | 27.211 | 597 | 0.01 |
| 15 | 27.467 | 75 | 0.00 |
| Totals | | 8858166 | 100.00 |

| Pk # | Retention Time | Area | Area Percent |
|---|---|---|---|
| 1 | 0.181 | 972 | 0.01 |
| 2 | 0.832 | 151 | 0.00 |
| 3 | 1.024 | 90 | 0.00 |
| 4 | 1.344 | 2870 | 0.03 |
| 5 | 1.749 | 64796 | 0.65 |
| 6 | 2.315 | 1365507 | 13.77 |
| 7 | 3.147 | 1821863 | 18.38 |
| 8 | 5.259 | 2164478 | 21.83 |
| 9 | 7.712 | 2734963 | 27.59 |
| 10 | 9.632 | 954070 | 9.62 |
| 11 | 13.824 | 500199 | 5.05 |
| 12 | 17.920 | 302406 | 3.05 |
| 13 | 20.736 | 1624 | 0.02 |
| 14 | 21.152 | 218 | 0.00 |
| 15 | 21.280 | 252 | 0.00 |
| 16 | 21.557 | 176 | 0.00 |
| Totals | | 9914635 | 100.00 |

| Pk # | Retention Time | Area | Area Percent |
|---|---|---|---|
| 1 | 1.333 | 7832 | 0.21 |
| 2 | 1.728 | 140502 | 3.71 |
| 3 | 2.251 | 1516820 | 40.10 |
| 4 | 3.019 | 802276 | 21.21 |
| 5 | 5.216 | 641251 | 16.95 |
| 6 | 7.591 | 672378 | 17.75 |
| 7 | 17.067 | 975 | 0.03 |
| 8 | 17.749 | 113 | 0.00 |
| 9 | 17.973 | 39 | 0.00 |
| Totals | | 3782196 | 100.00 |

BIOAVAILABILITY / BIOEFFICACY ENHANCING ACTIVITY OF *CUMINUM CYMINUM* AND EXTRACTS AND FRACTIONS THEREOF

This application claims the benefit of U.S. Provisional Application No. 60/363,460, filed Mar. 12. 2002 and incorporates the same by reference.

FIELD OF THE INVENTION

The present invention relates to a composition containing extract and/or bioactive fractions from the plant *Cuminum cyminum* as a bioavailability enhancer. The present invention also relates to a composition containing extract and/or bioactive fractions from the plant *Cuminum cyminum* with piperine as a bioavailability enhancer. The present invention in addition relates to the use of bioavailability and/or bioefficacy enhancers—also termed as bioenhancers or BE and methods of their preparation which include their isolation from a natural source and obtaining the final products in their chemically characterized or fingerprint-profiled form.

DESCRIPTION OF RELATED ART

Several approaches have been adopted in the past to maximize oral bioavailability, such as (a) particle size reduction (micronization, nanonization, etc.,) (b) polymorphic or crystal size and form selection, (c) solubilization of lesser soluble drugs by way of chemical modifications, complexation and use of co-solvents/surfactants, (d) targeted delivery of drug at the site of action, (e) controlled drug delivery by film coating or use of polymeric matrices for sustained release of drugs, (f) prodrug approach, and (g) microencapsulation using liposomes.

However, based on clues from Ayurvedic literature, a new approach of increasing the bioavailability of drugs including poorly-bioavailable drugs had been conceptualized at applicants institute Regional Research Laboratory (RRL), Jammu. One of the groups of herbals which has been documented very frequently as essential part of about 70% of Ayurvedic prescriptions, was noted to be 'Trikatu', that comprises three acrids viz. long pepper, black pepper and dry ginger in equal proportions. A single major alkaloidal constituent from peppers (piperine) was found to be responsible for bioavailability enhancing effect. The role of ginger is to regulate intestinal function to facilitate absorption. Influence of piperine was extensively studied on anti-TB drugs. It was determined that in combination with pipeline, the dose of rifampicin can be reduced by about 50% while retaining the therapeutic efficacy of this anti-TB drug at par with the standard dose (450 mg). Based on these findings several other reputed plants were evaluated for bioavailability/bioefficacy enhancing activity. Polar and non-polar extracts of parts of a few plants viz., *Zingiber officinale*, and *Carum carvi* increased significantly (25–300%), [Applicants co-pending patent applications] the bioavailability of a number of classes of drugs, for example, but not limited to, antibiotics, antifungals, anti-virals, anticancer, cardiovascular, CNS, anti-inflammatory/anti-arthritic, anti-TB/antileprosy, antihistaminic/respiratory disorders, corticosteroids, immunosuppressants, anti-ulcer. Such extracts either in presence or absence of piperine have been found to be highly selective in their bioavailability/bioefficacy enhancing action.

*Cuminum cyminum* (Linn.) (Umbelliferae) is a small, slender annual herb, which is grown extensively in South-Eastern Europe, North Africa bordering the Mediterranean-sea, in India and China. It is cultivated in almost all the states in India. The chief areas are reported to be U. P., Punjab, Rajasthan, Gujarat and Maharashtra. The plant prefers a mild climate and grows from sea level up to an elevation of 10,000 feet.

Its seeds have been used as an important condiment. In Ayurveda it is documented as katu, ushna and pacifies deranged vata. It is an effective gastric stimulant, beneficial in abdominal lump, flatulence, diarrhoea, sprue and a strong anthelmintic. It has therapeutically been used as an anti-diarrhoeal, galactagogue, diuretic and also beneficial in hoarseness of voice. It is also used as astringent, carminative. Paste of seeds when applied externally allays pain and irritation due to worms in the abdomen. Oil is useful in eczema.

Based on our past experience with the development of piperine as bioavailability enhancer from plants which are otherwise part of human diet and also documented to possess medicinal properties, we took up this plant to evaluate its bioavailability enhancing effect, if any, based on its attributes bearing some similarities to the plant sources of piperine.

Chemistry of *Cuminum cyminum*

The seeds of *Cuminum cyminum* were analyzed and it was reported that, analytical contents of seeds are (in percentage): moisture 11.9; protein 18.7; ether extractive 15.0; carbohydrates 36.6; fibre 12.0; mineral matter 5.8; calcium 1.08; phosphorus 0.49%; iron 31.0 mg/100 g; carotene calculated as vitamin A 870 1.U./100 gm; and vitamin C 3.0 mg/100 g (*Hlth Bull.*, No. 23, 1941,36).

The seeds on distillation yield a volatile oil (2.0–4.0%) having an unpleasant characteristic odour, spicy and somewhat bitter taste. The oil is colourless or yellow when fresh, turning dark on keeping. The analytical constants of the Indian oil are $d^{15°}$, 0.8945; $n_D^{25°}$ 1.490; $[\alpha]_D^{25°}$, +3.60; aldehydes 16%; the oil is soluble in 11 volume of 80% alcohol at 20° C. The ranges of constants reported by Parry are: sp. gr. 0.900–0.930;

n=1.494–1.507; [α]+3.0 to +8.0°; aldehydes 25–35% (Rao et al, *J. Indian Inst. Sci.*, 1925, 8A, 182; Parry, E. J. "The Chemistry of Essential Oils and Artificial Perfumes" [1921] (Scott, Greenwood & Son Ltd., London) Vol. 1, p. 311).

The chief constituent of the volatile oil is cuminaldehyde ($C_{10}H_{12}O$, p-isopropylbenzaldehyde, b.p. 2350), which forms nearly 20–40% of the oil. Besides the aldehyde, oil contains p-cymene, pinene, dipentene, cumene, cuminic alcohol, β-phellandrene and α-terpineol. The residue left after the volatile oil extraction contains 17.2% protein and 30.0% fat. It can be used as cattle feed (Finnemore, H. "The Essential Oils" [1926] (Ernest Benn. Ltd., London) p. 641). Besides volatile oil seeds contains 10% fixed oil, which is greenish brown in color with a strong aromatic flavor.

Other chemical constituents reported are apigenin-7-glucoside, apigenin-7,4'-diglucoside, apigenin-7,4'-diglucoside, apigenin-7-digalacturonide, apigenin-7-galacturonylglucoside, apigenin-7-digalacturonide-4'-glucoside, apigenin-6,8-di-C-glucoside, luteolin-glucoside, luteolin-7-diglucoside, luteolin-7,3'-diglucoside, luteolin-7,4'-diglucoside and luteolin-7-galacturonide-4'-glucoside and chrysoeriol glycoside [El-Negoumy, S. I. et al. *Grasas Aceites* (Seville) 1989, 40 (2) 87-9].

There is a great interest and medical need for the improvement of bioavailability of a large number of drugs, which are (a) poorly bioavailable, (b) administered for long periods, (c) toxic and (d) expensive. Maximizing oral bioavailability is therapeutically important because the extent of bioavailability directly influences plasma concentrations and consequently therapeutic efficacy and dose related toxic effects resulting after oral drug administration. Poorly bioavailable drugs remain sub-therapeutic because a major portion of a dose never reaches the plasma or exerts its pharmacological effect unless and until very large doses are given which may lead to serious side effects. Any significant improvement in bioavailability will result in lowering the dose or the dose frequency of that particular drug. Besides, inter-subject variability is inversely correlated with the extent of bioavailability. Therefore, low oral bioavailability leads to high variability and poor control of plasma concentration and pharmacodynamic effects. Inter-subject variability is particularly of concern for a drug with a narrow safety margin.

Incomplete oral bioavailability has various causes. These include poor dissolution or low aqueous solubility, poor intestinal membrane permeation, degradation of the drug in gastric or intestinal fluids and pre-systemic intestinal or hepatic metabolism. The normal practice to offset some of these problems has been to increase the dosage as stated earlier, which has the concerns of toxicity patients' non-compliance.

Many therapeutic treatments are also accompanied by loss of essential nutraceuticals in the course of therapy. The present invention improves nutritional status by increasing bioavailability/bioefficacy of various nutraceuticals also, which include metals and vitamins. The bioenhancers of the invention also have the potential to enhance the bioefficacy of a drug without influencing its plasma concentrations for various reasons, some of which, but not limited to, are described later in this invention under Section on 'Bioavailability/Bioenhancing activity'.

Bioavailability/Bioefficacy Enhancing Activity

In the present invention, the term Bioavailability or bioenhancing (BE) activity is defined as "a product at a lower dosage level which in combination with a drug or nutrient, provides more availability of the drug there by reducing the consumption of the drug or nutrient resulting in enhanced efficacy of the said drug.

In the present invention, the aqueous, aqueous—alcoholic, ketonic, ethereal, halogenated solvent extracts of the plant parts were evaluated with different therapeutic categories of drugs and nutraceutical (vital amino acids, metals, antioxidants, vitamins), and herbal drugs either alone or in combination. The bioavailability enhancing (BE) activity of the extracts was found to be consistent from 2.0 mg to 100 mg irrespective of the amount of the drug(s) present in the formulation. Sub-fractions of the extracts were also evaluated, with the same categories of drugs. The BE activity of the fractions increased corresponding to their proportions in the parent extract. The doses of the fractions responsible for the BE activity ranged from 0.5 to 25.0 mg. Both the fractions were found to be equally active within the above-mentioned range. Both the parent extracts as well as the fractions were found to be active individually as well as in combination with each other with different categories of drugs. The bioenhancer activity of the fraction (s) was found to be consistent from 0.5 mg to 25.0 mg irrespective of the amount of the drug(s) present in the formulation. The BE activity of the fractions was more enhanced as compared to that of the parent extracts.

The extracts or its fractions were found to be upto 50% more active when used individually in combination with piperine (1-piperoyl piperidine). Besides, both the parent extracts as wells as their fractions in different combinations showed almost similar enhanced activity upto 60% in presence of piperine. The amount of piperine in these formulations ranged from 3–20 mg.

The extracts or its fractions either in presence or absence of piperine have been found to be highly selective in their bioavailability enhancing activity. This is apparent from the degree of bioavailibility enhancement caused by these extracts/fractions. It varies from Nil to nearly significant (25%) to highly significant (435%). The reasons for this selective pattern may be attributable to one or more than one of the following reasons:

(a) Promoting the absorption of drugs from GIT,
(b) Inhibiting or reducing the rate of biotransformation of drugs in the liver or intestines,
(c) Modifying the immune system in a way that the overall requirement of the drug is reduced substantially,
(d) Increasing the penetration or the entry into the pathogens even where they become persistors within the macrophages such as for *Mycobacterium tuberculosis* and such others. This eventually ensures the enhanced killing of these organisms well secured within the places otherwise inaccessible to the active drug,
(e) Inhibiting the capability of pathogens or abnormal tissue to reject the drug e.g., efflux mechanisms frequently encountered with anti-malarial, anti-cancer and anti-microbial drugs,
(f) Modifying the signalling process between host and pathogen ensuring increased accessibility of the drugs to the pathogens,
(g) Enhancing the binding of the drug with the target sites such as receptors, proteins, DNA, RNA, and the like in the pathogen, thus potentiating and prolonging its effect leading to enhanced antibiotic activity against pathogens,
(h) Besides above plausible modes of action, the bioenhancer agents may also be useful for promoting the transport of nutrients and the drugs across the blood brain barrier, which could be of immense help in the control of diseases like cerebral infections, epilepsy and other CNS problems.

Primarily, but not exclusively, the invention enhances the carrier mediated entry of drugs and also the passive diffusion and the active transport pathways in the tissue which are responsible for transporting physiological substances such as nutraceuticals to their target sites. As applicable to any mechanism of action the products of this invention contribute in a synergistic and/or additive manner so that most drugs and nutraceuticals in presence of the products described in the present art are more bioavailable or bioefficaceous as a result of one or more of these mechanisms. The bioavailability and/or bioefficacy of drugs and nutraceuticals is also relevant to animal health besides being important for humans. The invention therefore is also intended to be used in veterinary preparations.

OBJECTS OF THE INVENTION

The main object of the invention is to provide an active of extract and bioactive fraction obtained from *Cuminum cyminum*.

Another object of the invention is to evaluate bioenhancing/bioavailability of *Cuminum cyminum* extract or bioactive fraction in combination with drugs, nutrients, nutraceuticals, micronutrients and herbal drugs/products.

Still another object of the invention is to provide a bioenhancer composition comprising active principles of

*Cuminum cyminum* in combination with drugs, nutrients, nutraceuticals, micronutrients and herbal drugs/products.

Still another embodiment of the present invention is to provide a bioenhancer composition comprising extract and/or bioactive fractions obtained from *Cuminum cyminum*, piperine and one or more selected from the group consisting of drugs, nutrients, nutraceuticals, micronutrients and herbal drugs/products.

Yet, another object of the invention is to provide a process for isolating bioactive factions from *Cuminum cyminum* useful as a bioenhancer.

Yet, another object of the invention is to provide a process for isolating bioactive faction from *Cuminum cyminum* using aqueous and/or alcoholic solvent

SUMMARY OF THE INVENTION

Accordingly, the present invention is directed to preparation of active extracts/fraction from the plant *Cuminum cyminum* which include their chemical characterization, fingerprint profiling and methods of using such products to enhance bioavailability and/or bioefficacy of drugs, natural products and essential nutraceuticals. The present invention is directed to preparation of composite bioenhancers comprising polar and non-polar extracts of parts of *Cuminum cyminum* and/or piperine (Ex: *Piper nigrum* and *Piper longum*) which increased significantly (25 to 435%), the bioavailability of a number of classes of drugs, for example, but not limited to, antibiotics, antifungals, anti-virals, anticancer, cardiovascular, CNS, anti-inflammatory/anti-arthritic, anti-TB/anti leprosy, anti-histaminic/respiratory disorders, corticosteroids, immunosuppressants, anti-ulcer. Such extracts/fractions of *C. cyminum* either in presence or absence of piperine (Ex: *Piper nigrum* and *Piper longum*) have been found to be highly selective in their bioavailability/bioefficacy enhancing action.

BRIEF DESCRIPTION OF THE ACCOMPANYING DRAWINGS

DETAILED DESCRIPTION OF THE INVENTION

Figure 1A:
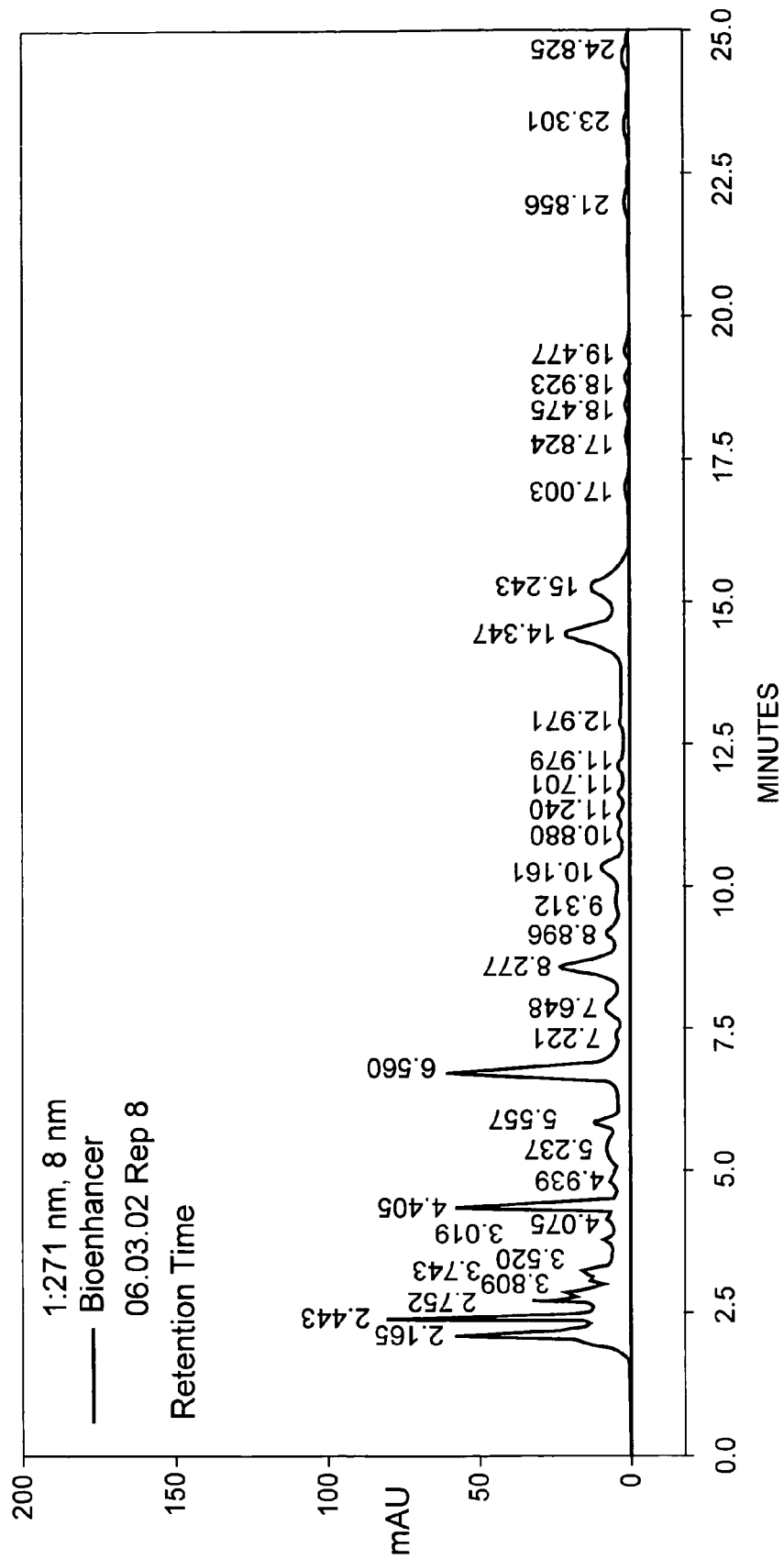
FIG. 1 represents HPLC chromatogram of aqueous extract of *Cuminum cyminum*
Figure 2A:
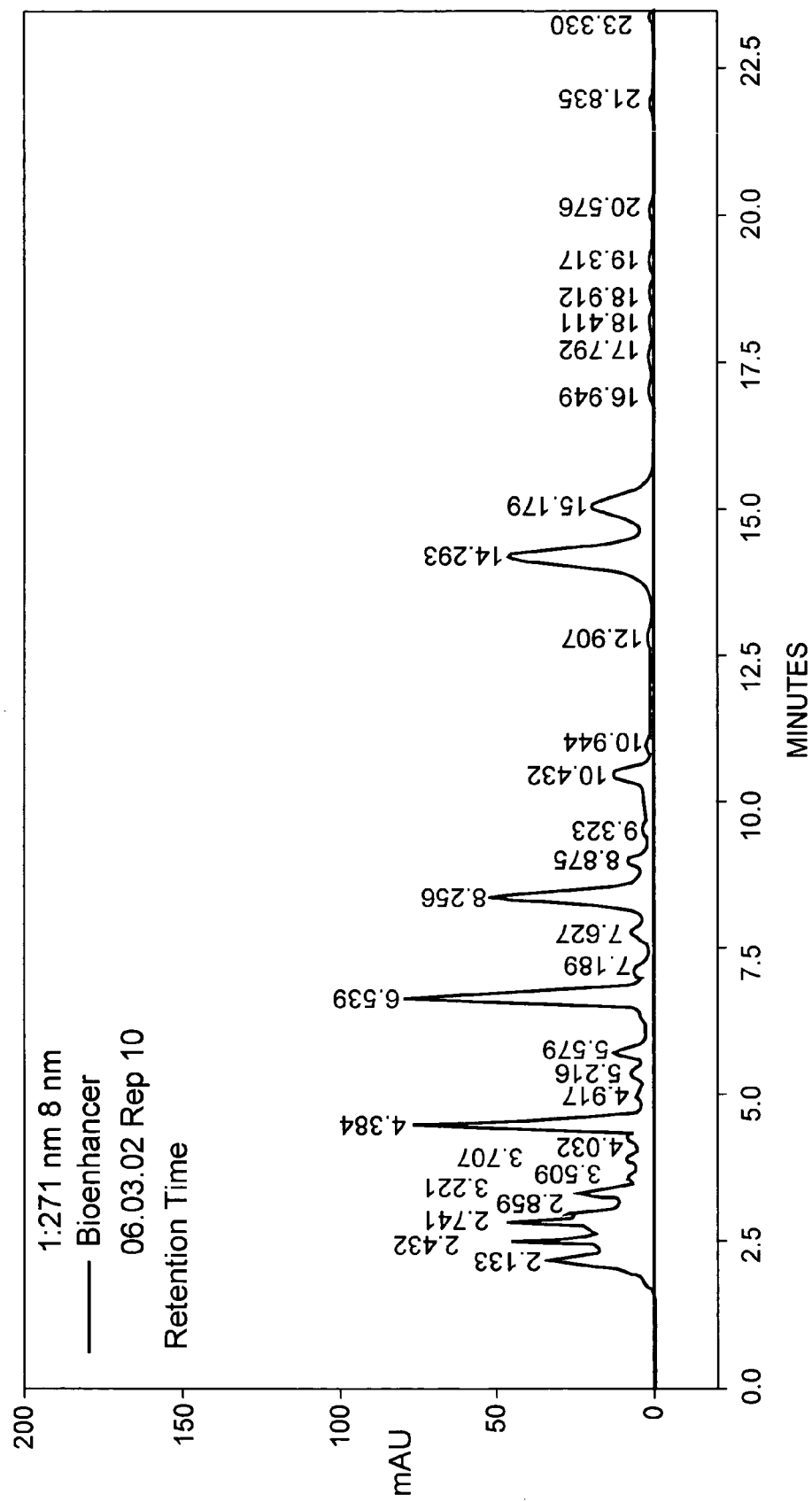
FIG. 2 represents HPLC chromatogram of 50% aqueous alcoholic extract of *Cuminum cyminum*
Figure 3A:
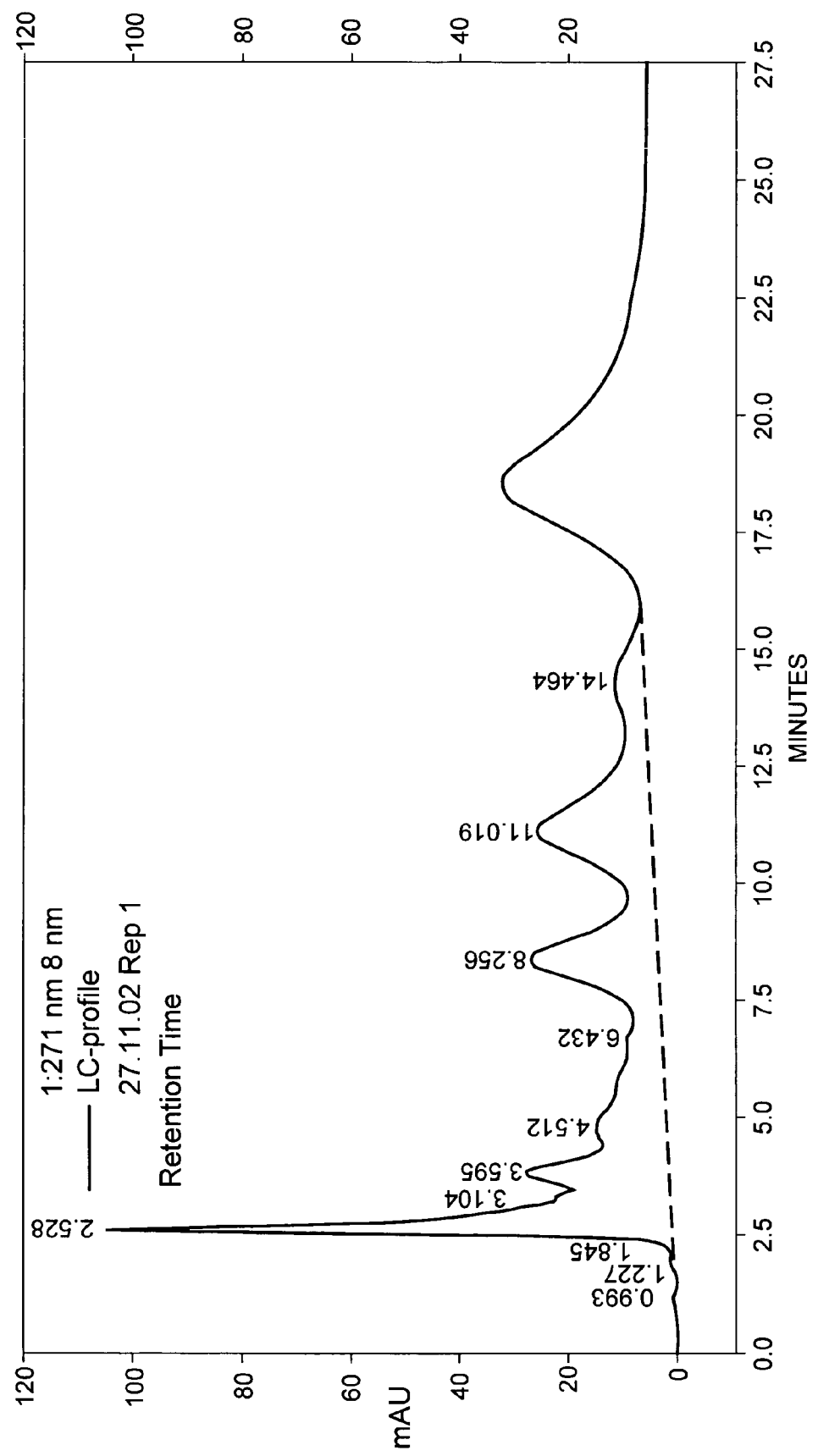
FIG. 3 represents HPLC chromatogram of fraction 1 of *Cuminum cyminum*
Figure 4A:
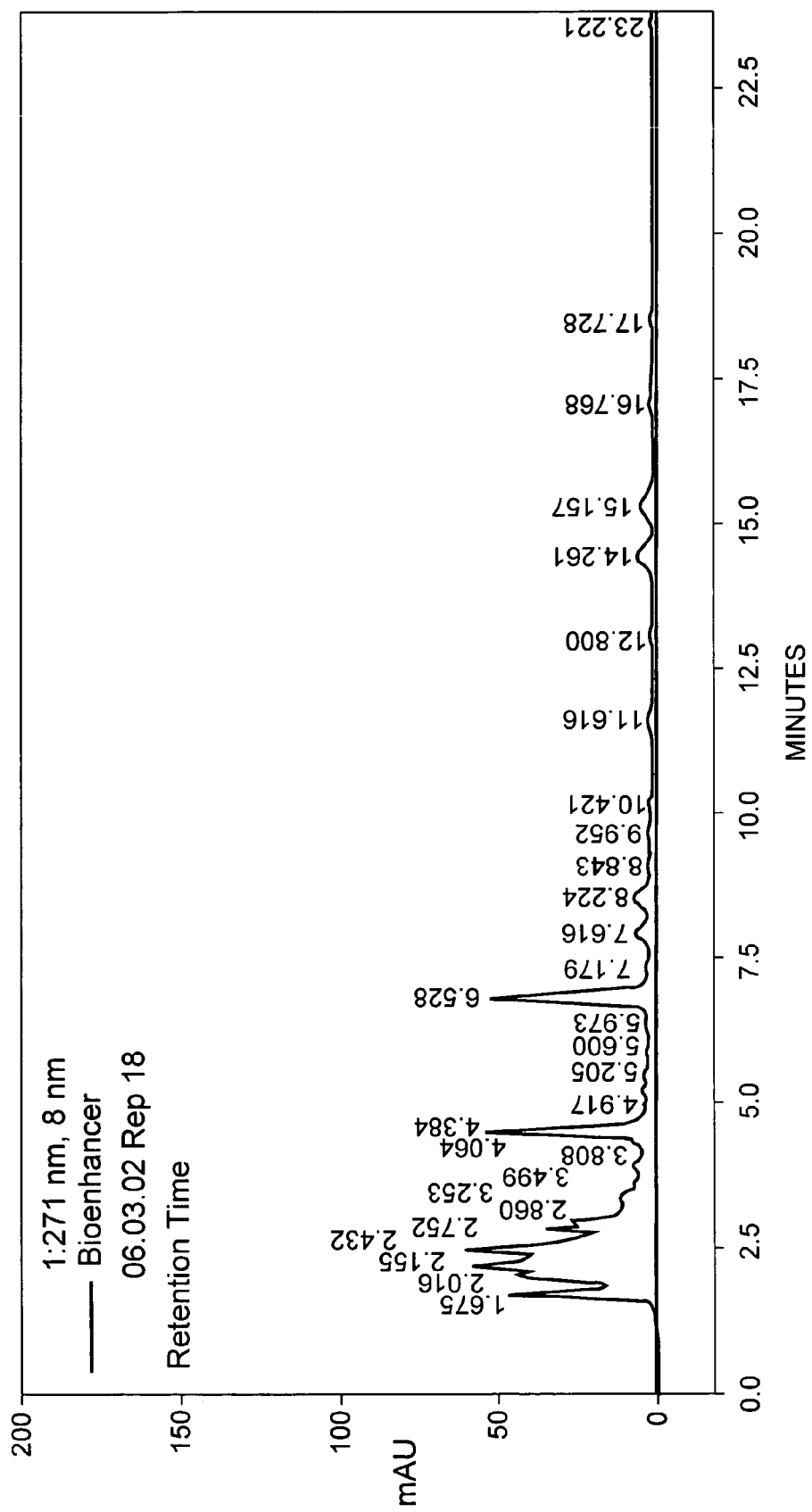
FIG. 4 represents HPLC chromatogram of fraction 2 of *Cuminum cyminum*
Figure 5A:
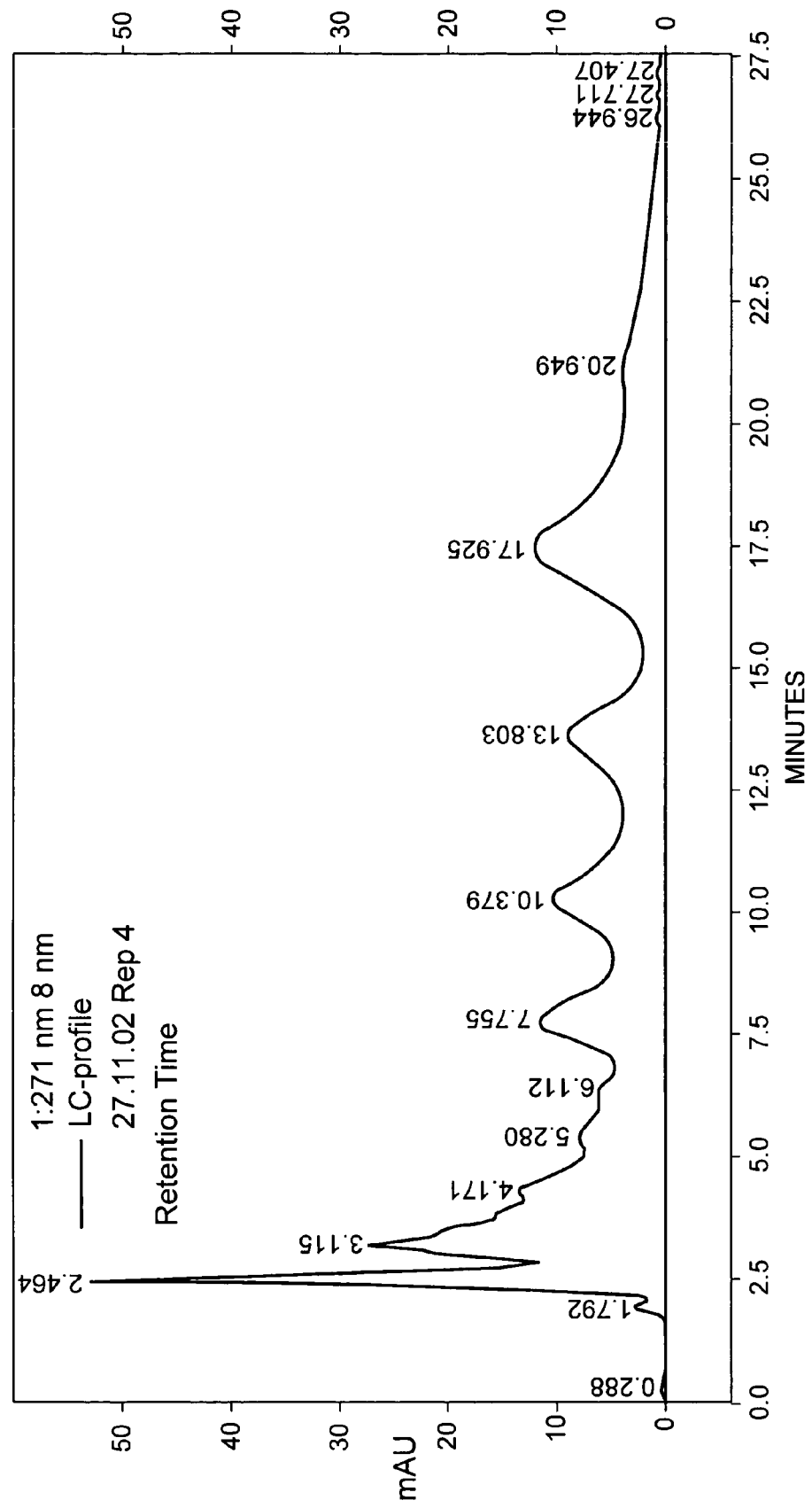
FIG. 5 represents HPLC chromatogram of fraction 3 of *Cuminum cyminum*
Figure 6A:
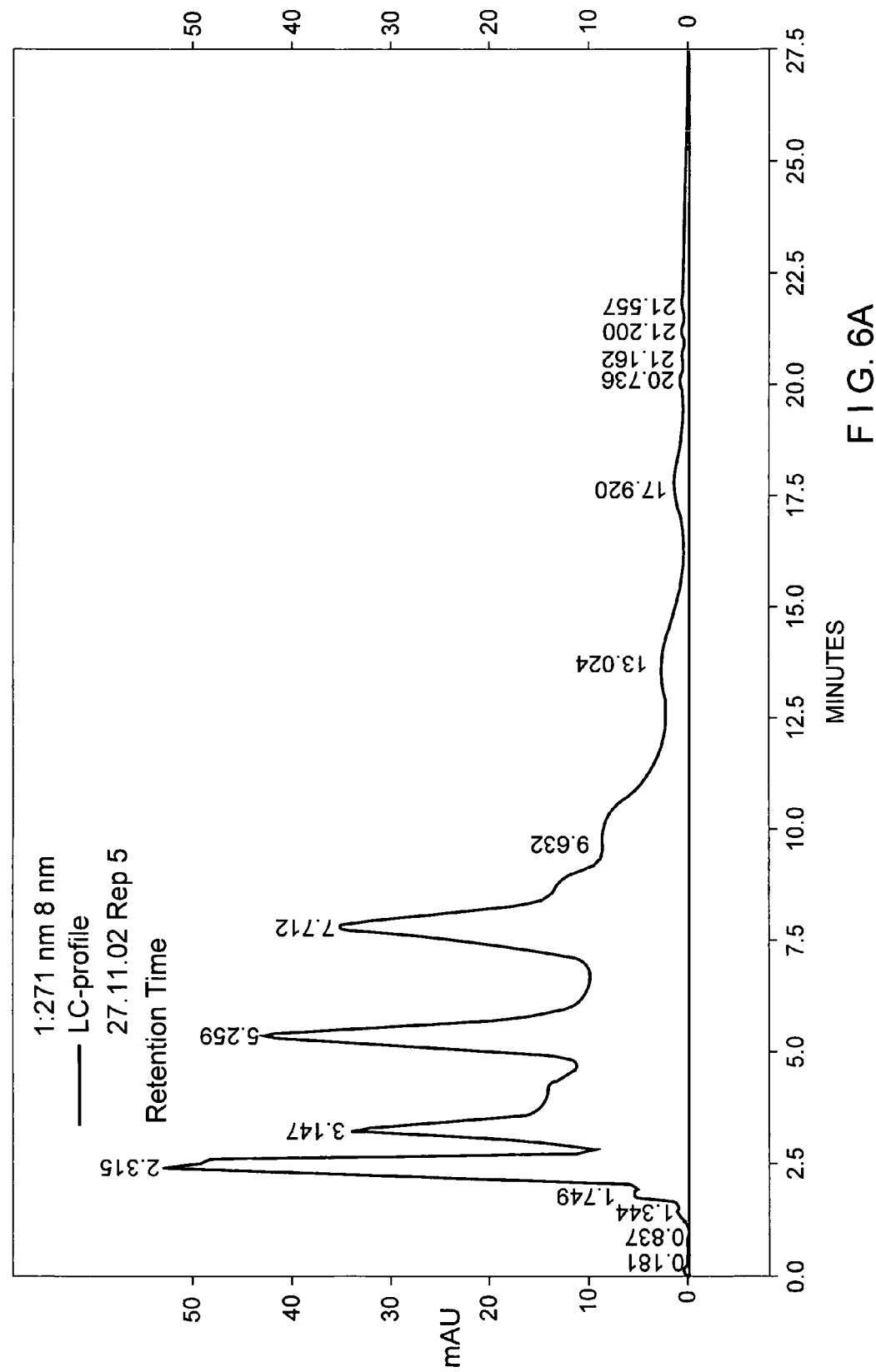
FIG. 6 represents HPLC chromatogram of fraction 4 of *Cuminum cyminum*
Figure 7A:
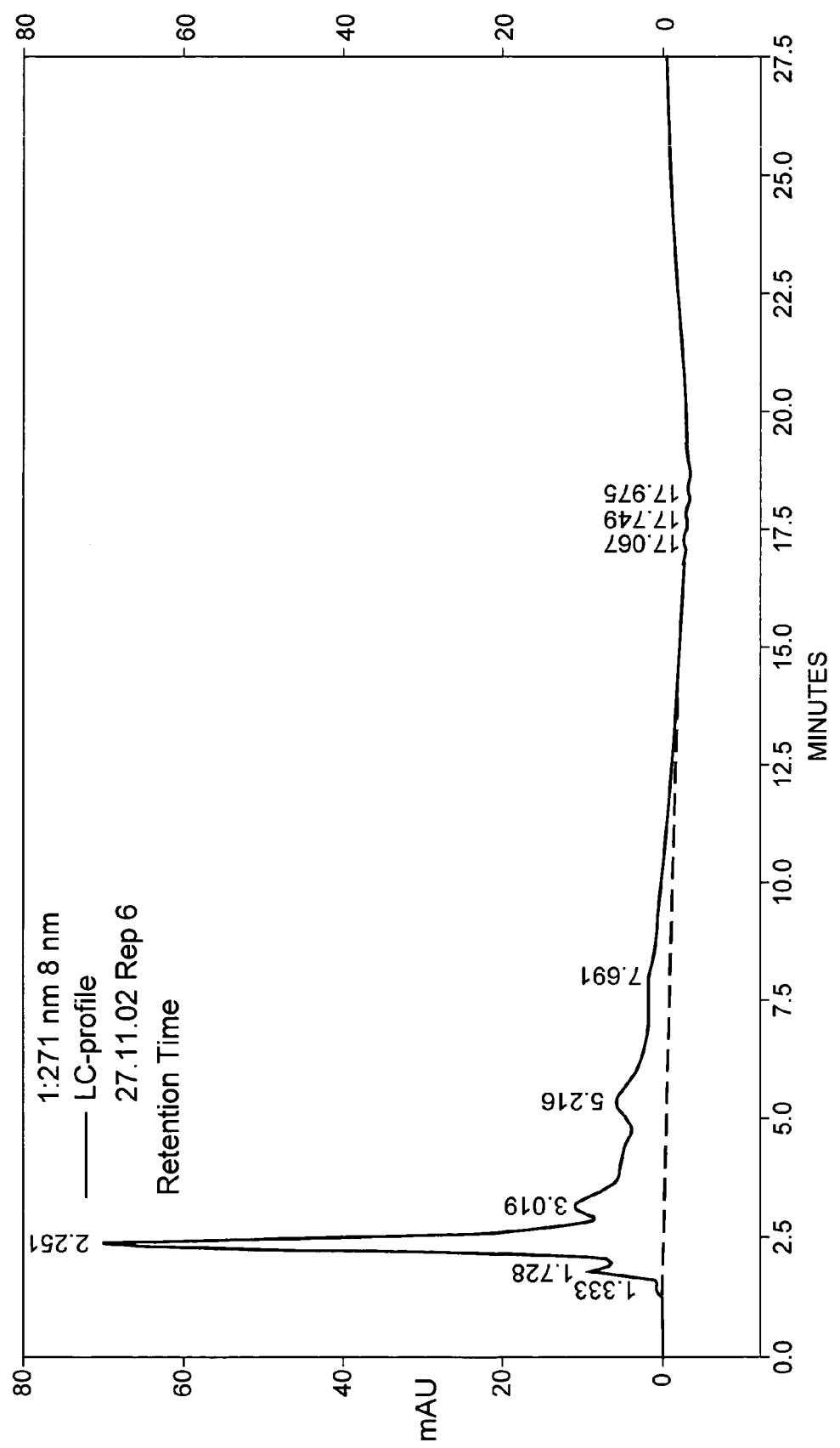
FIG. 7 represents HPLC chromatogram of fraction 5 of *Cuminum cyminum*

Accordingly, the present invention provides a bioenhancing/bioavailability-facilitating composition comprising:
  i. an effective amount of an extract and/or at least one bioactive fractions from *Cuminum cyminum*;
  ii. one or more additive selected from drugs, nutrients, vitamins, nutraceuticals, herbal drugs/products, micro nutrients, antioxidants along with pharmaceutically acceptable additives/excipient, and
  iii. optionally, an effective amount of piperine or extract/fraction of piper nigrum or piper longum.

One embodiment of the invention the amount of *Cuminum cyminum* extract used is in the range of about 1.0 to 250 mg, preferably in the range of 2.0 to 100 mg.

Another embodiment, the amount of *Cuminum cyminum* fraction used is in the range of about 0.5 to 75.0 mg irrespective of the amount of additive selected from drugs, nutrients, vitamins, nutraceuticals, herbal drugs/products, micro nutrients and antioxidants, preferably in the range of about 1.0 to 30 mg. The fraction *Cuminum cyminum* used is selected from fractions identified as 1 to 5

The amount of piperine used is in the range of about 3 to 50 mg, more particularly between 3 to 20 mg, wherein the piperine is isolated from piper nigrum, piper longum or its oleoresin.

Another embodiment of the invention provides a composition in which the drugs are selected from the group consisting of antibiotics, antifungal, antiviral, anticancer, cardiovascular, CNS drugs, anti-inflammatory/anti-arthritic, anti-TB/antileprosy drugs, anti-histamines/drugs for respiratory disorders, corticosteriods, immuno-suppressants, anti-ulcer drugs and herbal drugs.

Still another embodiment, the antibiotic used is selected from the group consisting of quinolones, macrolides, cephalosproins, penicillin and aminoglycosides; the quinolone is selected from the group consisting of Ciprofloxacin, Pefloxacin, Ofloxacin and Norfloxacin; the macrolide is selected from the group consisting of Erythromycin, Roxythromycin and Azithromycin; the cephalosproins is selected from the group consisting of Cefalexin, cefatrioxone, cefixime, Cefpirome, Cefdinir and Cefadroxil; the penicillin is selected from the group consisting of Amoxycillin and Cloxacillin; and the aminoglycocide is selected from the group consisting of Amikacin and Kanamycin.

Still another embodiment, the anti-fungal drug is selected from the group consisting of Fluconazole, Amphotericin B, Griseofulvin and Ketoconazole and the antiviral drug is selected from the group consisting of Acyclovir and Zidovudine.

Yet another embodiment, the anticancer drug is selected from the group consisting of Methotrexate, 5-Fluorouracil, Doxorubicin, Taxol and Cisplatin.

Another embodiment, the cardiovascular drug is selected from the group consisting of Amlodipin, Lisinopril, propranolol and Atenolol and CNS drugs is selected from the group consisting of Alprazolam and Haloperidol Still another embodiment anti-inflammatory/anti-arthritic drug is selected from the group consisting of Diclofenac, Piroxicam, Nimesulide and Rofecoxib and anti-TB/antileprosy drug is selected from the group consisting of Rifampicin, Ethionamide, Isoniazid, Cycloserine, Pyrazinamide, Ethambutol and Dapsone The antihistamine/drugs for respiratory disorders compound is selected from the group consisting of Salbutamol, Theophylline, Bromhexine and Loratidine; the corticosteriod is selected from the group consisting of Prednisolone, dexamethasone and Betamethasone; immuno-supressant is selected from the group consisting of Cyclosporin A, Tacrolimus and Mycophenolatemofetil and the anti-ulcer compound is selected from the group consisting of Rantidine, Cimetidine and Omerprazole.

Yet another embodiment the herbal product/drug is selected from *Echinacea, Tinospora cordifolia, Picrorrhiza kurroa, Aegles marmelos, Andrographis paniculata,*

*Emblica ribes, Asparagus racemosus, Terminalia chebula Withania somnifera, Centella asiatica* and/or their mixture thereof.

Another embodiment of the invention relates to a composition, wherein the nutrient is selected from group consisting of sugar, carbohydrates, fats and proteins, the vitamin is selected from the group consisting of Vitamin A, Vitamin E, Vitamin B1, Vitamin B6, Vitamin B12, Vitamin C and Folic acid; and the antioxidant is selected from the group consisting of β-Carotene, Silymarin, Selenium, Lycopene and Ellagiogallotannins Still another embodiment, natural herbal product is selected from the group consisting of Curcumin, Boswellic acids and Rutin and essential micro nutrients is selected from the group consisting of Methionine, Lysine, Leucine, Valine, Isoleucine, Zinc, Calcium, Glucose, Potassium, Copper and Iron Yet another embodiment, the plant extract of *Cuminum cyminum* or its bioactive fraction is extracted from any plant parts of *Cuminum cyminum*

In another embodiment, the above said composition is administered through oral, parenteral, nasal, inhalation including nebulisers, rectal, vaginal, transdermal and any others suitable routes.

In another embodiment, the bioenhancing effect of the extracts/fractions of *Cuminum cyminum* alone or in combination with piperine is selective in enhancing the bioavailability/bioefficacy of a drug, nutraceutical, and herbal drug/formulation.

One more embodiment of the invention provides the composition containing *Cuminum cyminum* extract or the fractions there of which provides bioavailability/bioenhancing activity in the range of 25–335%

Still another embodiment, the composition comprising components of *Cuminum cyminum* and piperine exhibit nearly significant i.e. about 25% to highly significant i.e. about 435% bioenhancing/bioavailability activity.

Yet another embodiment, the said composition-containing piperine and *Cuminum cyminum* provides further bioavailability/bio-enhancing activity in the range of 10 to 85% more than bioenhancing activity of *Cuminum cyminum* alone.

Another embodiment of the invention relates to the dosage level of the composition comprising *Cuminum cyminum* extract is in the range of 10 to 30-mg/kg/body weight and composition comprising bioactive fraction is in the range of 2 to 20-mg/kg/body weight.

Another embodiment of the invention relates to the dosage level of the composition comprising *Cuminum cyminum* extract or bioactive fraction along with piperine, wherein the dosage of piperine is in the range of 0 to 12-mg/kg/body weight.

One more embodiment of the present invention provides a process for the preparation of an aqueous extract, aqueous alcoholic extract and bioactive fraction from the plant *Cuminum cyminum*, said process comprises steps of:

a) extracting crushed plant material with water or 50% aqueous alcoholic solvent at a temperature range of 95–100° C. to obtain aq. extract or aq. alcoholic extract respectively, b) extracting a portion of aq. extrtact of step (a) with n-butanol (n-BuOH), separating the n-butanol layer and a aqueous layer, c) evaporating, freeze drying n-BuOH layer of step (b) to obtain fraction 1, d) evaporating, freeze drying the aq. layer of step (b) to obtain fraction 2, e) refluxing another portion of the aq.layer of step (a) with alcohol, pooling the alcohol extract and separating the residue left over, f) evaporating the pooled alcohol extract of step (e) to obtain a residue as fraction 3, g) extracting residue of step (e) with 50% aq.alcoholic solvent to obtain 50% aq.alcoholic soluble portion and residue as fraction 5, and h) evaporating the aqueous alocoholic soluble portion of step (g) to obtain a residue as fraction 4.

One more embodiment of the invention provides HPLC chromatogram for the extract and bioactive fractions obtained from plant *Cuminum cyminum*.

Still another embodiment, the HPLC chromatrogaph is obtained by using 2% acetic acid in water:acetonitrile in the ratio 83:17, RP18 column; flow rate 1 ml/minute using UV detector.

Another embodiment, the aqueous extract obtained from the plant *Cuminun cyminum* is having HPLC chromatograph major peaks with the retention time 2.16, 2.44, 4.40, 6.56, 8.27, 14.34 and 15.24.

Another embodiment, 50% aqueous alcoholic extract obtained from the plant *Cuminum cyminum* is having HPLC chromatograph peaks with the retention time 4.38, 6.53, 8.25, 10.43, 14.29 and 15.17.

Still another embodiment, fraction 1 obtained from the plant *Cuminum cyminum* is having HPLC chromatograph peaks with the retention time 2.52, 3.59, 6.25, 11.01 and 14.46.

Still another embodiment, fraction 2 obtained from the plant *Cuminum cyminum* has HPLC chromatograph peaks with the retention time 2.43, 4.38 and 6.52.

Still another embodiment, fraction 3 obtained from the plant *Cuminum cyminum* has HPLC chromatograph peaks with the retention time 3.11, 7.75, 10.37, 13.80 and 17.95.

Still another embodiment, fraction 4 obtained from the plant *Cuminum cyminum* has HPLC chromatograph major peaks with the retention time 2.31, 3.14, 5.25, 7.71, 9.63, 13.82 and 17.92.

Still another embodiment, fraction 5 obtained from the plant *Cuminum cyminum* has HPLC chromatograph major peaks with the retention time 2.25, 3.01, 5.21 and 7.69.

EXAMPLES

The following examples are intended to demonstrate some of the preferred embodiments and in no way should be construed so as to limit the scope of the invention. Any person skilled in the art can design more formulations, which may be considered as part of the present invention.

Example 1

Preparation of colourless, non-pungent piperine by a novel process as already claimed in IP 1726890 and further modified as follows: Commercially available *Piper nigrum* or *Piper longum* or their oleoresins have been used as the source material. 20 kg long pepper oleoresin is extracted with chlorinated solvents like $CHCl_3$, $CH_2Cl_2$, $C_2H_4Cl_2$ (25 litre) for six hours or 20 kg black pepper powder is Soxhletted with toluene for 8 hours. The extracts are concentrated to dryness under reduced pressure and dissolved in ethanol at 78° C. The ethanolic solution is adsorbed over neutral $Al_2O_3$ and packed in a glass column. Elution is carried out with $CHCl_3$: EtOH (9:1) and the eluate is concentrated to dryness and dissolved in minimum quantity of ethanol. The solution is treated with activated charcoal and filtered through a celite bed. The filtrate is concentrated to saturation point, cooled when colourless crystalline precipitate is obtained. The precipitate is separated by suction filtration and dried.

Example 2

The specifications of the preferred materials are as under:
Piperine
Colour: Colourless, monoclinic prismatic crystals;
Melting point: 129°–130° C.
Assay: Minimum 99.1% (LC/MS)
BE from *C. cyminum*
Preparation and fully fingerprinted (HPLC) products appended herewith as accompanying drawings.

Example 3

Doses, models/design of experiments and estimation methodology in a typical experiment is given below:

Doses of Different Bioenhancers Used and the Design of a Typical Experiment
1. Bioenhancers (BEs) from *Cuminum cyminum* means either the aqueous, or 50% alcoholic extract or fractions No. 1 to 5.
2. Piperine as Bioenhancer (BE) from Piper species means the molecule with characteristics as described in Example 2 of this invention.
3. In case of *Cuminum cyminum*, not withstanding the difference in dose of extract or its fraction, the enhancement caused in the bioavailability of the drug with which they are combined remains nearly the same, because the dose of the fraction used is proportionate to its concentration in the extract.
4. The doses remained either unchanged or were reduced by 50% even when the bioenhancers (BEs) were used in combination with each other.

Example 4

Doses (i) Bioenhancer (BE) from *Cuminum cyminum*
   Extract: 16 mg/kg body weight (Rats)
   Fraction No. 1: 02–5 mg/kg body weight (rats)
   Fraction No.2: 13-mg/kg body weight (Rats)
   Fraction No. 3: 8 mg/kg body weight (Rats)
   Fraction No. 4: 5 mg/kg body weight (Rats)
   Fraction No. 5: 2.5 to 5 mg/kg body weight (Rats)
(ii) Piperine: 8 mg/kg body weight (Rats)

As an example of an experiment in Rat (fasted):
   Drug: Rifampicin, 40 mg/kg
   BE (*Cuminum cyminum*): Doses as in Example No. 5 above.
   BE (*Cuminum cyminum*)+Piperine: Doses as in Example No. 5 above.
   Experimental procedure: Drug alone/or in combination with BE was administered to rats as per the following design:
   Group 1: Control
   Group 2: Rifampicin alone
   Group 3: BE alone
   Group 4: Rifampicin+BE (*Cuminum cyminum*)
   Group 5: Rifampicin+BE (*C. cyminum*+piperine)
   Blood from control/treated animals at predetermined intervals (0–24 hrs) (Total 14 timings). Rifampicin was extracted from the blood (plasma) using dichloromethane. The concentration of rifampicin in the samples was determined using HPLC (Model: Shimadzu 1080 BP); PDA detector; Mobile phase: phosphate buffer: acetonitile (40: 60); Flow rate 1.0 ml/min. Column RP 18.
   Control and BE only groups were employed to study the interference of plasma component and the bioenhancer used.

Example 5

The above methodology was adapted for evaluating the bio-enhancing activity of other drugs, micro nutrients, nutracuticals, nutrients and other herbal products and the enhancing effects are tabulated under each heading. List of drugs, nutraceuticals, herbal formulations cited below as some of the example for the purpose of present invention.

| | A. Drugs | |
|---|---|---|
| | Categories | Drugs |
| I | Antibiotics | Fluoroquinolones |
| | | Cipro-, Nor-, P-, and 0-floxacins |
| | | Macrolides |
| | | Erythro-, Roxythro-, and Azithromycin |
| | | Cephalosporins |
| | | Cefalexin, Cefadroxil, cefatrioxone, Cefixime, Cefpirome, Cefdinir |
| | | Penicillins |
| | | Amoxycillin, Cloxacillin |
| | | Aminoglycosides |
| | | Amikacin, Kanamycin |
| II. | Antifungal | Fluconazole, Amphotericin B, Ketoconazole, Griseofulvin |
| III. | Anti-viral | Acyclovir, Zidovudine |
| IV. | Anti-cancer | Methotrexate, 5-Fluorouracil, Doxorubicin Cisplatin |
| V. | Cardiovascular drug | Amlodipin, Lisinopril & Atenolol |
| VI. | CNS drugs | Alprazolam & Haloperidol |
| VII | Anti-inflammatory/ antiarthritic (NSAID) | Diclofenac, Piroxicam, Nimesulide & Rofecoxib |
| VIII | Anti-TB/Antileprosy drugs | Rifampicin, Ethionamide, Isoniazid, Cycloserine Pyrazinamide, Ethambutol Dapsone |
| IX. | Anti histamines/ respiratory disorders | Salbutamol, Theophylline, Bromhexine, Loratidine |
| X. | Corticosteroids | Prednisolone, dexamethasone, Betamethasone |
| XI. | Immuno-suppressants | Cyclosporin A, Tacrolimus, Mycophenolate mofetil |
| XII | Antiulcer | Ranitidine, cimetidine, omeprazole |

A. Drug Categories:

I. Antibiotics:
(a) Fluroquinolones

% Enhancement in bioavailability

| Drug | BE from *Cuminum cyminum* | Piperine as BE | Piperine + Active molecule |
|---|---|---|---|
| Ciprofloxacin | 52 | 40 | 47 |
| P-floxacin | 47 | 51 | 57 |
| O-floxacin | 61 | 40 | 73 |
| Norfloxacin | Negligible | Negligible | Negligible |

(b) Macrolides

% Enhancement in bioavailability

| Drug | BE from *Cuminum cyminum* | Piperine as BE | Piperine + Active molecule |
|---|---|---|---|
| Erythromycin | 75 | 105 | 95 |
| Roxythromycin | 67 | 95 | 103 |
| Azithromycin | 83 | 91 | 97 |

(c) Cephalosporins

% Enhancement in bioavailability

| Drug | BE from *Cuminum cyminum* | Piperine as BE | Piperine + BE from *Cuminum cyminum* |
|---|---|---|---|
| Cefalexin | 60 | 70 | 75 |
| Cefadroxil | 90 | 86 | 79 |
| Cefatrioxone | Nil | Nil | Nil |
| Cefixime | Nil | Nil | Nil |

(d) Penicillins

% Enhancement in bioavailability

| Drug | BE from *Cuminum cyminum* | Piperine as BE | Piperine + Active molecule |
|---|---|---|---|
| Amoxycillin | 75 | 111 | 98 |
| Cloxacillin | 94 | 68 | 95 |

(e) Aminoglycosides

% Enhancement in bioavailability

| Drug | BE from *Cuminum cyminum* | Piperine as BE | Piperine + Active molecule |
|---|---|---|---|
| Amikacin | Nil | Negligible | Nil |
| Kanamycin | 95 | 65 | 110 |

II. Antifungal

% Enhancement in bioavailability

| Drug | BE from *Cuminum cyminum* | Piperine as BE | Piperine + Active molecule |
|---|---|---|---|
| Fluconazole | 170 | 110 | 126 |
| Amphotericin B | Nil | Negligible | negligible |
| Ketoconazole | 136 | 138 | 156 |

III. Anti-viral

% Enhancement in bioavailability

| Drug | BE from *Cuminum cyminum* | Piperine as BE | Piperine + Active molecule |
|---|---|---|---|
| Acyclovir | 110 | 77 | 98 |
| Zidovudine | 330 | 270 | 415 |

IV. CNS drugs

% Enhancement in bioavailability

| Drug | BE from *Cuminum cyminum* | Piperine as BE | Piperine + Active molecule |
|---|---|---|---|
| Alprazolam | 60 | 98 | 104 |
| Haloperidol | Nil | Nil | Nil |

IV. Anti-cancer

% Enhancement in bioavailability

| Drug | BE from *Cuminum cyminum* | Piperine as BE | Piperine + Active molecule. |
|---|---|---|---|
| Methotrexate | 125 | 70 | 30 |
| 5-Fluorouracil | 335 | 290 | 435 |
| Doxorubicin | 85 | 42 | 103 |
| Cisplatin | 70 | Negligible | 79 |

VI. Cardiovascular drugs

% Enhancement in bioavailability

| Drug | BE from *Cuminum cyminum* | Piperine as BE | Piperine + Active molecule |
|---|---|---|---|
| Amlodipine | 55 | 29 | 103 |
| Lisinopril | 83 | 110 | 98 |
| Atenolol | Nil | Negligible | Negligible |
| Propranolol | 135 | 170 | 210 |

VII. Anti-inflammatory/antiarthritic

% Enhancement in bioavailability

| Drug | BE from *Cuminum cyminum* | Piperine as BE | Piperine + Active molecule. |
|---|---|---|---|
| Diclofenac | 65 | 79 | 108 |
| Piroxicam | 70 | 92 | 107 |
| Nimesulide | 168 | 110 | 150 |
| Rofecoxib | Negligible | Negligible | Negligible |

VIII. Anti-TB/Antileprosy drugs

% Enhancement in bioavailability

| Drug | BE from Cuminum cyminum | Piperine as BE | Piperine + Active molecule. |
|---|---|---|---|
| Rifampicin | 250 | 115 | 366 |
| Isoniazid | Nil | 22 | Negligible |
| Pyrazinamide | Nil | 17 | Nil |
| Ethambutol | Nil | Nil | Nil |
| Dapsone | 60 | 40 | 75 |
| Ethionamide | 78 | 48 | 65 |
| Cycloserine | 89 | 50 | 90 |

IX. Anti-histamines/respiratory disorders

% Enhancement in bioavailability

| Drug | BE from Cuminum cyminum. | Piperine as BE | Pipenne + Active molecule |
|---|---|---|---|
| Salbutamol | 110 | 55 | 85 |
| Theophylline | 87 | 70 | 75 |
| Bromhexine | 50 | 48 | 90 |
| Loratidine | Nil | Nil | Nil |

X. Corticosteroids

% Enhancement in bioavailability

| Drug | BE from Cuminum cyminum. | Piperine as BE | Piperine + Active molecule |
|---|---|---|---|
| Prednisolone | Nil | Nil | Nil |
| Dexamethasone | 85 | 56 | 105 |
| Betamethasone | 95 | 65 | 82 |

XI. Immunosuppressants

% Enhancement in bioavailability

| Drug | BE from Cuminum cyminum | Piperine as BE | Piperine + Active molecule |
|---|---|---|---|
| Cyclosporin A | 156 | 223 | 275 |
| Tacrolimus | 75 | 105 | 117 |
| Mycophenolate Mofeit | Nil | Nil | Nil |

XII. Anti-ulcer

% Enhancement in bioavailability

| Drug | BE from Cuminum cyminum. | Piperine as BE | Piperine + BE Cuminum cyminum. |
|---|---|---|---|
| Ranitidine | 117 | nil | 89 |
| Cimetidine | 123 | Nil | 105 |
| Omeprazole | Nil | Nil | Nil |

B. Nutraceuticals

% enhancement in bioavailability

| Category | Dose (mg/kg) | BE from Cuminum cyminum | Piperine | Piperine + BE from C. cyminum |
|---|---|---|---|---|
| I. Vitamins | | | | |
| Vitamin A | 1 | 26 | 14 | 18 |
| Vitamin E | 40 | Nil | Nil | Nil |
| Vit. B1 | 10 | 37 | 16 | 33 |
| Vit. B6 | 0.5 | Nil | Nil | Nil |
| Vit B12 | 0.1 ug | Nil | Nil | Nil |
| Vit. C | 50 | Nil | Nil | Nil |
| Folic acid | 50 ug | Nil | Nil | Nil |
| II. Antioxidants | | | | |
| β-Carotene | 15 | 45 | 34 | 53 |
| Silymarin | 5 | 32 | 13 | 41 |
| Selenium | 2 | Nil | Nil | Nil |
| III. Natural herbal products | | | | |
| Curcumin | 50 | 39 | 33 | 29 |
| Boswellic acids | 50 | Nil | Nil | Nil |
| Rutin | 40 | Nil | 26 | 22 |
| IV. Essential nutritional components | | | | |
| Methionine | 20 | 27 | 23 | 30 |
| Lysine | 40 | 35 | 31 | 29 |
| Leucine | 50 | 31 | 25 | 32 |
| Valine | 25 | 20 | 26 | 24 |
| Isoleucine | 25 | 40 | 18 | 22 |
| Zinc* | 0.1 | Negligible | Nil | Nil |
| Calcium* | 30 | 17 | Negligible | Negligible |
| Glucose | 50 | 16 | 29 | 11 |
| Potassium* | 25 | Nil | Nil | Nil |
| Copper* | 30 | Nil | Nil | Nil |
| Iron* | 0.5 | 23 | Nil | 29 |

*Doses equivalent to elemental concentration and estimated by Atomic Absorption Spectrometry

C. Herbal formulations

% Enhancement in bioavailability/bioefficacy

| Drug | BE from Cuminum cyminum. | Piperine as BE | Piperine + BE from C. cyminum |
|---|---|---|---|
| Echinacea | 72 | 110 | 90 |
| Tinospora cordifolia | 98 | 107 | 152 |
| Picrorrhiza kurroa | 78 | 95 | 115 |
| Aegles marmelos | Nil | Nil | Nil |
| Andrographis paniculata | 72 | Nil | 68 |
| Emblica ribes | 72 | Nil | 60 |
| Asparagus racemosus | 35 | 47 | 72 |
| Terminalia chebula | Nil | Nil | Nil |
| Withania somnifera | 55 | 52 | 65 |
| Centella asiatica | Nil | Nil | Nil |

Flow Sheet for Preparation of Extracts of Plant *Cuminum Cyminum*

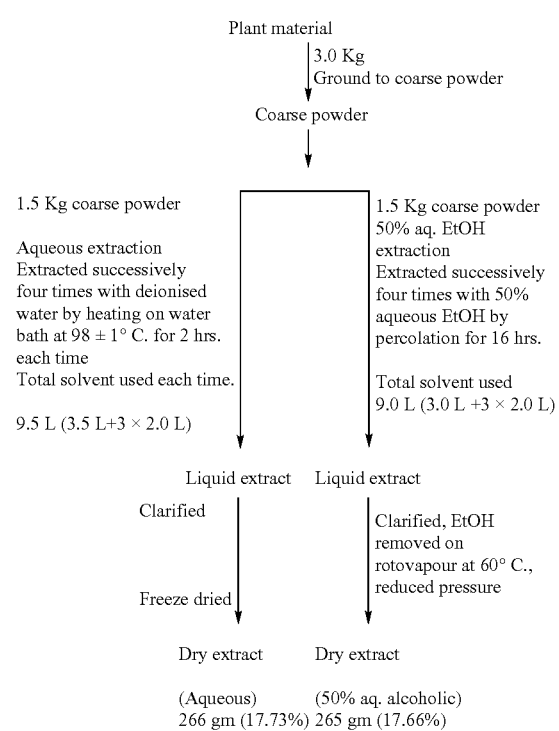

Flow Sheet for Fractionation of Aqueous Extract of *Cuminum Cyminum*

Bioactivity Guided Fractionation of Aqueous Extract was Carried out as Typical Example by Partitioning with n-BuOH and H₂O (SCHEME 1) and Triturating Another Portion of Extract with 95% EtOH, 50% Aq. EtOH (SCHEME-2)

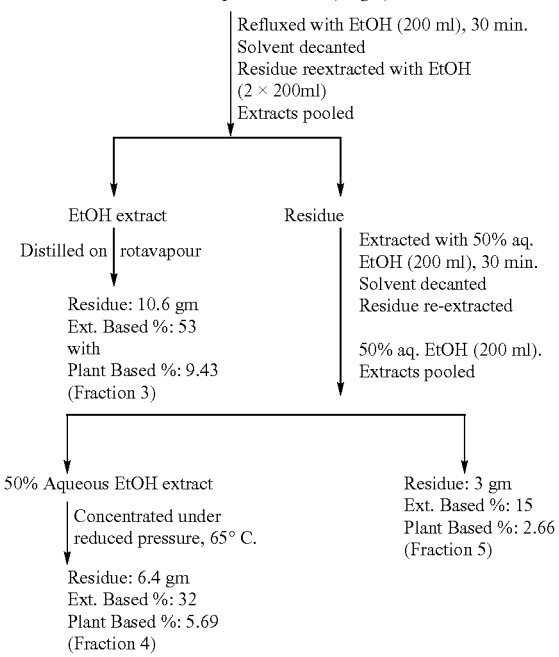

The original 50% aq. alcoholic extract of the plant material can also be fractionated by the same scheme as above.

The original 50% aq. alcoholic extract of the plant material can also be fractionated by scheme as mentioned above.

The invention claimed is:

1. A composition for enhancing the bioavailability or bioefficacy of a drug, nutrient, vitamin, nutraceutical, herbal drug, herbal product, micro nutrient or antioxidant; comprising: i) an effective amount of an extract selected from the group consisting of fraction 1, fraction 2, fraction 3, fraction 4 and fraction 5 from *Cuminum cyminum*; said extract prepared by the process comprising
   a) extracting crushed plant material of *Cuminum cyminum* with water or 50% aqueous alcoholic solvent at a temperature range of 95–100° C. to obtain an aqueous extract or aqueous alcoholic extract respectively, and
   b) extracting a portion of the aqueous extract of step a) with n-butanol (n-BuOH), separating the n-butanol layer and an aqueous layer;
   c) evaporating and freeze drying the n-butanol layer of step b) to obtain fraction 1; or
   d) evaporating and freeze drying the aqueous layer of step (b) to obtain fraction 2; or
   e) refluxing a portion of the aqueous extract of step a) with alcohol, pooling the alcohol extract and separating the residue left over, and
   f) evaporating the pooled alcohol extract of step e) to obtain a residue as fraction 3; or
   g) extracting the residue of step (e) with 50% aqueous alcoholic solvent to obtain 50% aqueous alcoholic soluble portion and residue, said residue comprising fraction 5; or
   h) evaporating the aqueous alcoholic soluble portion of step (g) to obtain a residue fraction 4;
   i) one or more additives selected from the group consisting of drugs, nutrients, vitamins, nutraceuticals, herbal drugs, herbal products, micro nutrients, and antioxidants; and a pharmaceutically acceptable additive, excipient or a mixture thereof, and iii) optionally, an effective amount of piperine, or an extract of *Piper nigrum* or *Piper longum*.

2. The composition as claimed in claim 1, wherein the amount of *Cuminun cyminum* extract within said composition is in the range of about 1.0 to 250 mg.

3. The composition as claimed in claim 2, wherein the amount of *Cuminum cyminum* extract within said composition is between 2.0 to 100 mg.

4. The composition as claimed in claim 1, wherein the amount of *Cuminum cyminum* extract within said composition is in the range of about 0.5 to 75.0 mg irrespective of the amount of additive in the composition.

5. The composition as claimed in claim 1, wherein the amount of *Cuminum cyminum* extract within said composition is in the range of about 1.0 to 30 mg.

6. The composition as claimed in claim 1, wherein the amount of piperine within said composition is in the range of about 2 to 50 mg.

7. The composition as claimed in claim 1, wherein the piperine is isolated from *piper nigrum, piper longum* or its oleoresin.

8. The composition as claimed in claim 1, wherein the plant extract of *Cuminum cyminum* is obtained from any part of *Cuminum cyminum*.

9. The composition as claimed in claim 1, wherein said composition is administered through oral, parenteral, nasal, inhalation including nebulisers; rectal, vaginal, transdermal or any other suitable route.

10. The composition as claimed in claim 1, wherein the bioenhancing effect of the extract of *Cuminum cyminum* alone or in combination with piperine is selective in enhancing the bioavailability, bioefficacy or both of a drug, nutraceutical, herbal drug or herbal formulation.

11. The composition as claimed in claim 1, wherein the composition containing the *Cuminum cyminum* extract provides bioavailability or bio-enhancing activity in the range of 25–335%.

12. The composition as claimed in claim 1, wherein said composition-containing piperine and *Cuminum extract cyminum* provides further bioavailability/bio-enhancing activity in the range of 10 to 85% more than the bioenhancing activity of *Cuminum extract cyminum* alone.

13. The composition as claimed in claim 1, wherein the amount of *Cuminum cyminum* extract within a dosage form is in the range of 10 to 75-mg/kg/body weight.

14. The composition as claimed in claim 1, wherein the amount of piperine is in the range of 0 to 12-mg/kg/body weight.

15. The composition as claimed in claim 1, wherein the drug is selected from the group consisting of antibiotics, antifungal, antiviral, anticancer, cardiovascular, CNS drugs, anti-inflammatory, anti-arthritic, anti-TB, anti-leprosy drugs, anti-histamines, drugs for respiratory disorders, corticosteriods, immuno-suppressants, and anti-ulcer drugs.

16. The composition as claimed in claim 15, wherein the antibiotic is selected from the group consisting of quinolones, macrolides, cephalosporins, penicillin and aminoglycosides.

17. The composition as claimed in claim 16, wherein the quinolone is selected from the group consisting of ciprofloxacin, pefloxacin, ofloxacin and norfloxacin.

18. The composition as claimed in claim 16, wherein the macrolide is selected from the group consisting of erythromycin, roxythromycin and azitbromycin.

19. The composition as claimed in claim 16, wherein the cephalosporin is selected from the group consisting of cefalexin, cefatrioxone, cefixime, cefpirome, cefdinir and cefadroxil.

20. The composition as claimed in claim 16, wherein the penicillin is selected from the group consisting of Amoxycillin and Cloxacillin.

21. The composition as claimed in claim 16, wherein the aminoglycoside is selected from the group consisting of amikacin and kanamycin.

22. The composition as claimed in claim 15, wherein anti-fungal drug is selected from the group consisting of fluconazole, amphotericin B, griseofulvin and ketoconazole.

23. The composition as claimed in claim 15, wherein antiviral drug is selected from the group consisting of acyclovir and zidovudine.

24. The composition as claimed in claim 15, wherein anticancer drug is selected from the group consisting of methotrexate, 5-fluorouracil, doxorubicin, taxol and cisplatin.

25. The composition as claimed in claim 15, wherein cardiovascular drug is selected from the group consisting of amlodipine, lisinopnl, propranolol and atenolol.

26. The composition as claimed in claim 15, wherein CNS drug is selected from the group consisting of alprazolam and haloperidol.

27. The composition as claimed in claim 15, wherein the anti-inflammatory or anti-arthritic drug is selected from the group consisting of diclofenac, piroxicam, nimesulide and rofecoxib.

28. The composition as claimed in claim 15, wherein anti-TB or anti-leprosy drug is selected from the group consisting of rifampicin, ethionamide, isoniazid, cycloserine, pyrazinamide, ethambutol and dapsone.

29. The composition as claimed in claim 15, wherein antihistamine or drug for a respiratory disorder is selected from the group consisting of salbutamol, theophylline, bromhexine and loratidine.

30. The composition as claimed in claim 15, wherein corticosteriod is selected from the group consisting of prednisolone, dexamethasone and betamethasone.

31. The composition as claimed in claim 15, wherein immuno-supressant is selected from the group consisting of Cyclosporin A, tacrolimus and mycophenolatemofetil.

32. The composition as claimed in claim 15, wherein the anti-ulcer compound is selected from the group consisting of rantdine, cimetidine and omeprazole.

33. The composition as claimed in claim 1, wherein the herbal product or herbal drug is selected from *Echinacea, Tinospora cordifolia, Picrorrhiza kurroa, Aegles marmelos, Andrographis paniculata, Emblica ribes, Asparagus racemosus, Terminalia chebula, Withania somnifera*, and *Centella asiatica* or a mixture thereof.

34. The composition as claimed in claim 1, wherein the nutrient is selected from group consisting of sugar, carbohydrates, fats and proteins.

35. The composition as claimed in claim 1, wherein the vitamin is selected from the group consisting of Vitamin A, Vitamin E, Vitamin B1, Vitamin B6, Vitamin B12, Vitamin C and Folic acid.

36. The composition as claimed in claim 1, wherein the antioxidant is selected from the group consisting of .beta.-Carotene, Silymarin, Selenium, Lycopene and Ellagiogallotannins.

37. The composition as claimed in claim 1, wherein the herbal product is selected from the group consisting of Curcumin, Boswellic acids and Rutin.

38. The composition as claimed in claim 1, wherein the essential micro nutrient is selected from the group consisting of Methionine, Lysine, Leucine, Valine, Isoleucine, Zinc, Calcium, Glucose, Potassium, Copper and Iron.

* * * * *

UNITED STATES PATENT AND TRADEMARK OFFICE
CERTIFICATE OF CORRECTION

PATENT NO.        : 7,070,814 B2
APPLICATION NO.   : 10/386395
DATED             : July 4, 2006
INVENTOR(S)       : Ghulam Nabi Qazi et al.

Page 1 of 1

It is certified that error appears in the above-identified patent and that said Letters Patent is hereby corrected as shown below:

On title page, item 75, line 7, "Absullah" should read -- Abdullah --.

Signed and Sealed this

Twenty-second Day of May, 2007

JON W. DUDAS
*Director of the United States Patent and Trademark Office*